US00PP13418P2

(12) United States Plant Patent
Mukherjee et al.

(10) Patent No.: US PP13,418 P2
(45) Date of Patent: Dec. 24, 2002

(54) GLADIOLUS HYBRID PLANT NAMED 'PALAMPUR QUEEN'

(75) Inventors: Devashish Mukherjee, Palampur (IN); Devendra Dhayani, Palampur (IN); Jaichand Rana, Simla (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/815,605

(22) Filed: Mar. 23, 2001

(51) Int. Cl.[7] ..... A01H 5/00
(52) U.S. Cl. ..... Plt./301
(58) Field of Search ..... Plt./301

*Primary Examiner*—Bruce R. Campell
*Assistant Examiner*—Annette Para
(74) *Attorney, Agent, or Firm*—Renner, Otto, Boisselle & Sklar, LLP

(57) ABSTRACT

The invention relates to a novel and distinct hybrid plant named 'Palampur Queen' (*Gladiolus sp*) characterized by its attractive Capsicum red colored flowers with Chartreuse red color on the lip petals.

1 Drawing Sheet

FIELD OF THE INVENTION

Figure 1:
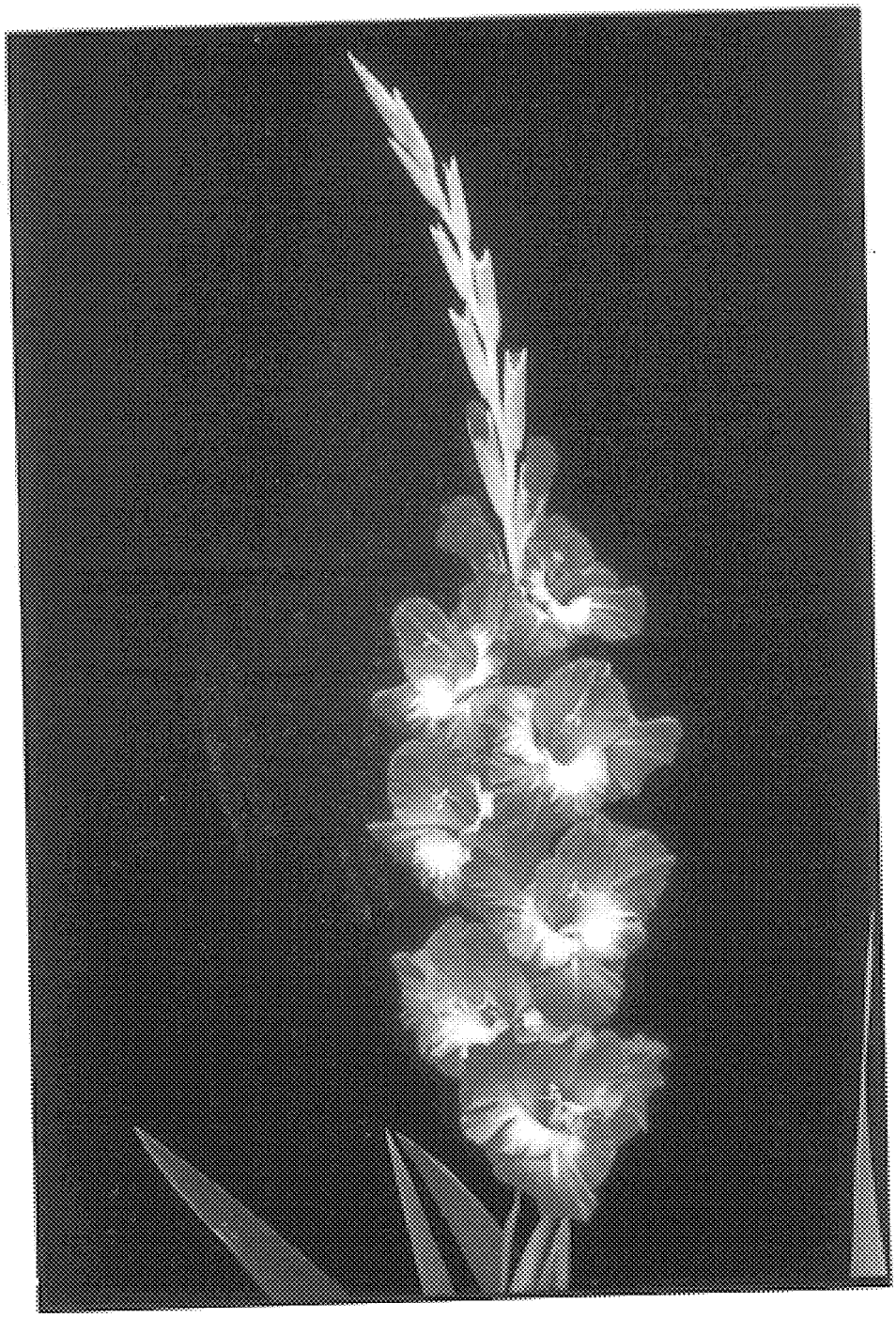

The present invention relates to a novel hybrid plant named 'Palampur Queen' and belonging to the family Iridaceae. The novel plant being a hybrid, has been developed in a breeding program. The novel plant 'Palampur Queen' is propagated vegetatively by corms and hence can be maintained as a stable genotype. The plant of the invention is an ornamental plant widely cultivated for beautiful flowers which are of commercial and export value.

LATIN NAME

The Latin name of the novel hybrid plant of the present invention is *Gladiolus sp.*

REPRODUCTION AND STABILITY

The seedling named 'Palampur Queen' produced one corm and 11 cormels in the first year after harvesting. The corm and cormels were sown in a field during the next growing season. The cornmels became flowering size corms within a year. Again in the next year corms and cormels were sown in a field to produce a large number of corms and cormels. This process was repeated in subsequent years to increase the corm and cormel population.

The above method is the asexual reproduction used to propagate 'Palampur Queen'.

The hybrid 'Palampur Queen' has remained stable and uniform for its morphological characters and showed consistency in performance for various growth and flowering parameters during its evaluation and vegetative multiplication since 1992. Throughout the evaluation period of 'Palampur Queen' no variants were found from the normal population. The genotype 'Palampur Queen' was bred at the Institute of Himalayan Bioresource Technology (IHBT) under the program of development of new varieties of gladiolus.

BACKGROUND OF THE INVENTION

The present invention relates to a new and distinct variety of gladiolus, a member of the Gladiolus genus. The novel plant is the hybrid between the gladiolus plants Green Woodpecker and Oscar which are hybrid varieties. The Green Woodpecker and Oscar hybrid varieties have been in cultivation in India for more than 20 years and are believed to be un-patented in the United States. Additionally, the Green Woodpecker and Oscar hybrid varieties are not known to be the subject of any currently pending U.S. patent applications.

Gladiolus is one of the important cut flowers throughout the world. The commercial cultivation is wide spread in temperate, tropical and subtropical climates. The demand of new varieties with better color, quality flowers, and planting materials is always existing in the floriculture trade.

The modern garden cultivators gladiolus come from diverse genetic parentages. It has cumulative heterozygosity for many characters inherent with complex genetic constitution. In gladiolus, diverse parents are crossed together and the cultivars and the species that differ widely in chromosome numbers are also cross-fertile. In the present invention, the desirable strains obtained in $F_1$ generation were perpetuated vegetatively without being segregated in the following generations, so that the cultivars which are available today may be $F_2$, $F_3$ to $F_8$ or so of a particular cross further blended with some extra parents at nearly every generation. Thus they are not allowed to segregate freely in further generations because it is desirable to grow the plants asexually. Because of this reason, now the available modern cultivars have become so complex that the offspring obtained by crossing them, even two seedlings, do not appear similar [(Misra, 1975) Gladiolus Br. Assn. Newsletter, No. 12, pp. 2–5].

The Applicants collected germplasm of different cultivars and hybrid varieties of gladiolus from National Botanical Research Institute Lucknow, India as per the list of gladiolus cultivars grown in India and described in the bulletin of 'gladiolus' Economic Botany Information Service by Sharma et al. published by the Director National Botanical Research Institute Lucknow, 1988. Germplasm of gladiolus was also collected from Netherlands in 1991 and various nurseries of Kalimpong, Darjeeling, West Bengal, India. The record of the collected germplasm of gladiolus was maintained in the accession register of the Floriculture Division of the Institute of Himalayan Bioresource Technology (IHBT), Palampur, India.

The applicants initiated a breeding program to develop better types of gladiolus hybrids suitable to wide range of climatic conditions, and having wide range of characteristics such as better color, increased number of florets and spike length as per the international standards, better yield of corms and cormels, tolerant to the common diseases etc. The collected germplasm of gladiolus was planted in the experimental field of IHBT for their propagation and multiplication. In this breeding programme conventional breeding method (hybridization) was used. More than 100 cross combinations were made by using distinct varieties such as Oscar, Jester, Snow Princess, Eurovision, Ballerina, King Liar, Cherry Blossom, Her Majesty, Green woodpecker, Friendship, Vink's Glory, Aldebaran, Red Beauty, Top Brass, Copper King, Bonfire, White Goddess, Sunny Boy, Tropic Sea and Friendship Pink etc.

Flower color description of some of the parentage as described in NAGC Bulletin.

Oscar: Turkey red, throat blotched sulphur yellow.

Green Woodpecker: Pea green, throat blotched pea green spotted ruby red.

Eurovision: Signal red, throat streaked pea green.

Friendship pink: Dawn pink, throat blotched pea green having splashes ruby red.

Aldebaran: Straw yellow and throat bloched signal red.

As the aim is the production of seed of known parentage, emasculation in first three flowers in a selected spike is done before the opening of the flowers and stigma becomes receptive. Anthers are removed carefully from each flower. Emasculated flowers were covered with butter paper bags used for breeding purposes. Pollination was done in the emasculated flowers next day morning with in 24–30 hours with the pollens of the desired parents in the month of April–May 1991. The seeds were collected from mature pods in the month of August–September and were sown in beds under open field conditions and covered with dry grasses for moisture preservation in December 1991. The resultant seedlings were space planted in the field at Palampur in March–April 1992.

Many seedlings came out from a single cross combination. These plants were critically evaluated and tagged as per the desired color combinations, growth and flowering parameters. The corn and cormels of the selected hybrid plants were replanted continuously four years in the filed for further evaluation and multiplications. Based on the superior performance for attractive color combination, compactness of flower spike, number of flowers per spike, length of flower spike, number of corm and cormels per plant evaluation and selection of superior quality hybrids were made.

Thus, the breeding program involved hybridization of commonly available gladiolus plants. In other words, the hybrids were developed by crossing parental genotypes involving sexual hybridization in the breeding program.

The program yielded a number of hybrid plants out of which one genotype, namely IHBT-GH-425, was selected and christened as 'Palampur Queen'. This plant was found to have new color, flower size, number of florets per spikes, length of flower spikes, better yield of corm and cormels and less prone to common diseases. Growing the plant on a commercial scale offers the horticulturists an improved and new variety, which can be commercially cultivated.

DETAILED DESCRIPTION OF THE INVENTION

Thus, the invention provides a new genotype christened as 'Palampur Queen'. This plant has been developed through planned breeding experiments conducted at Institute of Himalayan Resources, (IHBT) Palampur, Himachal Pradesh, India with defined aim to develop superior gladiolus genotypes. For this purpose, gladiolus varieties were collected from different sources and grown in the fields at Palampur, India for facilitating breeding program. The emasculation and pollination in different varieties were carried out during the months of April–May 1991. The seeds were collected in July–August 1991 and sown in beds under open field conditions and covered with dry grasses in December 1991. The resultant seedlings were space planted in the field at Palampur in March–April 1992. The corms and cormels of surviving hybrid plants were replanted continuously four years for screening and multiplication.

Based on the superior performance for attractive color combination, compactness of flower spikes, number of flowers per spikes, length of flower spikes, number of flowers remains open at a time, number of corm and cormel production per plant, the plant of this invention, the 'Palampur Queen', was selected for further observation and evaluation.

Considering the superior characteristics like excellent color, number of flowers, compactness of flower spikes, plant height, ruffled-ness of flower petals, regeneration potential and freedom from common diseases, it was asexually reproduced through corm and cormels to maintain purity.

The selected hybrid was christened as 'Palampur Queen' and grown at row distance of 1 feet and plant to plant distance of 6 inches for four consecutive years to study its growth and flowering performance and multiplication. Data were recorded on randomly selected twenty plants every year. The 'Palampur Queen' maintained uniformity in its growth and flowering performance.

With regard to the age and the growing conditions of the 'Palampur Queen', the present hybrid was raised in the calendar year 1991 through conventional breeding and the age of the hybrid is presently in excess of ten years. The hybrid was grown under open field conditions in the Palampur area of Himachal Pradesh. The altitude of the Palampur area is about 1300 meters above sea level. The climate zone of the region is sub-humid, sub-temperate, having maximum and minimum average temperatures of 30° C. and 10° C. The average annual rainfall in the region is approximately 250 cm.

EVIDENCE OF UNIFORMITY AND STABILITY

The hybrid 'Palampur Queen' has remained stable and uniform for its morphological characters and showed consistency in performance for various growth and flowering parameters during its evaluation and vegetative multiplication since 1992. Throughout the evaluation period of 'Palampur Queen' no variants were found from the normal population.

The genotype 'Palampur Queen' possesses decorative type flowers of Capsicum red (RHS-33A) with Chartreuse yellow (RHS-2D) color on lip petals. The flower petals are slightly ruffled which is quite clear from FIG. 1.

The genotype 'Palampur Queen' is distinct in regeneration potential.

BRIEF DESCRIPTION OF THE ACCOMPANYING PHOTOGRAPH

FIG. 1 is a photograph of a field grown flower spike of the 'Palampur Queen' depicting decorative type flowers of Capsicum red (RHS-33A) with Chartreuse yellow (RHS-2D) color on lip petals.

SUMMARY OF THE INVENTION

The plant of invention 'Palampur Queen' is thus a new and distinct hybrid plant, having the following combination of characters:

(a) Color flowers of Capsicum red (RHS-33A) with Chartreuse yellow (RHS-2D) color on lip petals;

(b) Ruffled petals;

(c) Average days to flower: about 93 days;

(d) Average number of flower spikes/plant is 1.47;

(e) Average length of flower spikes is 138 cm; and (f) Average number of flowers per spikes is 18.5.

DETAILED BOTANICAL DESCRIPTION

The following is an objective description of the new variety.

1. Genus: Gladiolus.
2. Species: Hybrid sp.
3. Family: Iridacae.
4. Common name: Sward lily/gladiolus.
5. Average plant height: 153.95 cm.
6. Growth habit: Erect, uniform.
7. Average stem diameter: 1.39 cm.
8. Average number of leaves/plant: 8.0.
9. Average height of leaves: 74.58 cm.
10. Average days to flower: 93 days.
11. Leaves: Numerous, cauline, alternatively overlapping, sheathing at the base; blades linear—lanceolate, flattened, sword shape, 32 to 110 cm in length from ground level (average 74.06 cm) and 4.2 to 9.5 cm in width (average 6.5 cm), base cuneate, apex acute or acuminate, margin entire, sinuate, both upper and lower surfaces glabrous. Scabrid due to prominent venation, ventral surface more darker (RHS-137B) than the dorsal surface, venation parallel, multicostate, convergent type, veins prominent, white, thick and fibrous.
12. Type of flowers: Decorative.
13. Bud size: Buds are 6.54 cm to 9.69 cm long (bottom 3 buds were measured), average size 7.48 cm in length, the diameter of the lower 3 buds ranges from 0.78 cm to 1.46 cm, with the average being 1.11 cm.
14. Bud color: Bud color is red (RHS-44A).
15. Average number of spikes/plant: 1.47.
16. Average length of the flower spike: 138 cm.
17. Average number of flowers/spike: 18.5.
18. Flower color: Capsicum red (RHS-33A) with Chartreuse yellow (RHS -2D) color on lip petals.
19. Type of petals: Petals ruffled.
20. Average number of flowers that remain open at a time: 7.94.
21. Average longevity of the 1st flower: 3.72 days.
22. Average diameter of 1st flower: 10.2 cm.
23. Flow fragrance: No fragrance.
24. Average longevity of the spike: 10.3 days.
25. Average number of corms/plant: 1.52.
26. Average diameter of corms: 7.29 cm.
27. Average number of cormels/plant: 46.
28. Reproductive organs:
    *Androecium.*—Stamens triandrous to pentandrous (i.e., 3 to 5 in number), mostly triandous, epiphyllous, adnate to tubular base of perianth segments; filaments free or slightly connate at the base, arranged in a whorl, 2.7 cm long, slightly curved, shorter than perianth segments, pink-white; anthers 2-lobed, extrose, dorsifixed, 1.3 cm long, pink violet.
    *Gynoecium.*—Ovary inferior, tricarpellary, syncarpus, triocular, many ovules in each locule, placentation axile, style single, terminal, slightly curved, white-pink, 8.0 cm long; stigma petaloid, trilobed, stalked, each lobe slightly folded, globose, shining, pink colored, middle lobe larger than lateral ones, bifid, lobe margins wavy, oblique, lobe 4 mm long, lobe stalks 3 mm long.

The gladiolus plant of the present invention is commercially propagated vegetatively through corms and cormels. The average diameter of the corm of the 'Palampur Queen' is 6 to 7 cm. The 'Palampur Queen' color is entirely different than that of its parents the Green Woodpecker and the Oscar. The flower of 'Palampur Queen' is Capsicum Red with Chartreuse Yellow color on the lip petal. The flower color of the Green Woodpecker is Pea Green, throat blotched pea green spotted ruby red. The flower color of the Oscar is Turkey Red, throat blotched sulphur yellow.

The production of gladiolus through cormels is the asexual method of propagation for reproducing planting material.

The color specifications of the flower parts distinguishing Palampur Queen from others within the same botanical and market class have been incorporated according to R.H.S. Colour Chart published by The Royal Horticultural Society, 80 Vincent Square, London S W1P 2PE, 1995. The distinguishing characteristics are compared with other cultivars of same botanic and market class emphasize the distinctiveness of 'Palampur Queen'.

We claim:

1. A new and distinct cultivar of gladiolus plant named 'Palampur Queen', as illustrated and described.

* * * * *